United States Patent [19]

Shepherd et al.

[11] Patent Number: 4,781,705
[45] Date of Patent: Nov. 1, 1988

[54] MINERAL APPLICATOR

[75] Inventors: Charles G. Shepherd, Oakville; Margaux A. Greenhouse, Toronto, both of Canada

[73] Assignee: Zyton Inc., Toronto, Canada

[21] Appl. No.: 62,618

[22] Filed: Jun. 16, 1987

[51] Int. Cl.$^4$ ............... A61M 35/00; A61F 13/00
[52] U.S. Cl. ................... 604/289; 604/304; 128/897 X; 63/3
[58] Field of Search ............ 128/1 R, 796; 604/289, 604/304; 63/1.1, 2, 3

[56] References Cited

U.S. PATENT DOCUMENTS

| | | | |
|---|---|---|---|
| 1,238,872 | 9/1917 | Bell | 604/289 X |
| 2,510,224 | 6/1950 | Hettinger | 63/3 X |
| 4,078,660 | 3/1978 | Lerro | 128/1 R X |

*Primary Examiner*—Allen M. Ostrager
*Attorney, Agent, or Firm*—George A. Rolston

[57] ABSTRACT

A mineral applicator adapted to be worn on the person and having a holder body adapted to be placed against the skin, a retaining device for retaining the holder body on the skin, and a plurality of mineral objects on the holder body for contacting the skin.

5 Claims, 2 Drawing Sheets

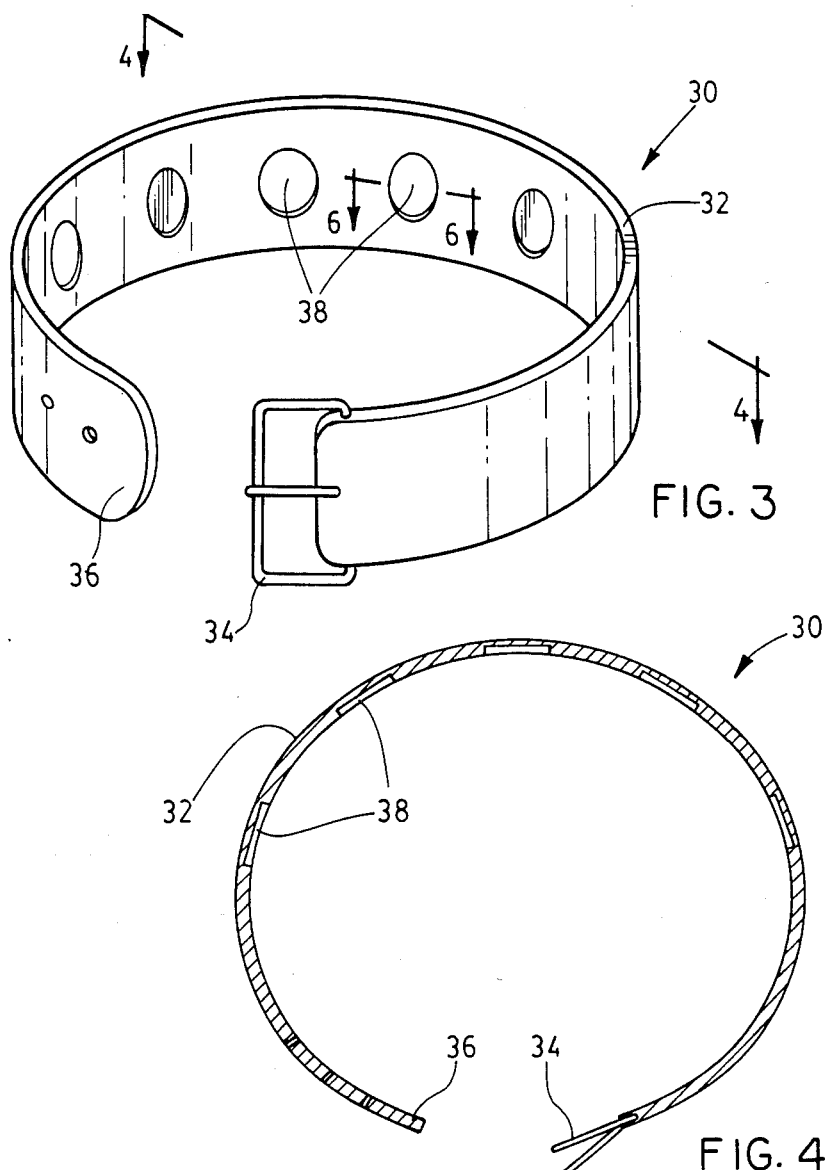
FIG. 3
FIG. 4
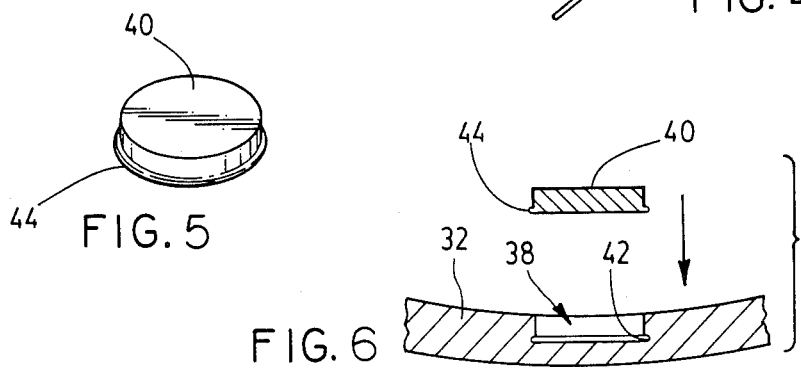
FIG. 5
FIG. 6

MINERAL APPLICATOR

The invention relates to a mineral applicator for holding mineral objects against the skin, such as a wrist band, ankle strap or the like, and includes a plurality of mineral objects supported by such an applicator.

BACKGROUND OF THE INVENTION

It is well known that some persons wish to wear a metallic object against their skin. A typical example is the well known copper bracelet. It is believed by such persons that the metal from the object in some way or another leaches into the skin, and beneficial results are claimed by such persons as a result of wearing the object.

Bracelets and other objects of various different sizes and shapes have been worn for the purpose.

Other metals, such as zinc, iron and the like, and other non-metallic minerals such as calcium etc., are also considered beneficial and are often taken internally.

It is a general objection of the invention to provide a mineral applicator such as a bracelet, ankle strap or the like, which incorporates a plurality of mineral objects, and holds them against the skin.

By varying and by increasing or reducing the number of such mineral objects, the wearer can vary the minerals to suit his or her wishes.

It is a further general objective of the invention to provide such a mineral applicator with a plurality of mineral objects formed of or containing or incorporating different minerals or elements whereby the skin may be contacted by several different minerals or elements simultaneously. In this way, if a person chooses to do so he or she may wear such a holder with a selection of different mineral objects, applying different minerals or elements to the skin simultaneously, and may vary the proportions of different minerals or elements, by varying the number of such mineral objects.

BRIEF SUMMARY OF THE INVENTION

With a view to achieving the foregoing objectives, the invention comprises a mineral applicator having a holder body with a contact surface adapted to be placed against the skin, engagement means on said holder body, adjacent said contact surface, retaining means for retaining said holder body on the skin and a plurality of mineral objects engageable with said engagement means, said mineral objects being supported adjacent said contact surface of said holder body, for contacting the skin.

More particularly, the invention provides a mineral applicator having the foregoing advantages in which said holder body is formed around an arc, to fit around a portion of the body, and wherein said contact surface is on the inside of said arc.

More particularly, the invention seeks to provide a mineral applicator having the foregoing advantages, wherein said engagement means comprise a plurality of recesses formed in said contact surface at spaced intervals.

More particularly, the invention seeks to provide a mineral applicator having the foregoing advantages wherein said mineral objects comprise a plurality of metal members of identical shape and size, at least some of said members being coated with a coating of copper, and some of said members being coated with a coating of zinc.

More particularly, it is an objective of the invention to provide such a mineral applicator wherein the user may readily exchange some of the mineral objects for others, thereby enabling a selection to be made of a specific combination of numbers and types of mineral objects.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

FIG. 3 is a perspective illustration of a further embodiment of mineral applicators;

FIG. 4 is an enlarged section along the line 4—4 of FIG. 3;

FIG. 5 is a perspective illustration of a mineral object, and,

FIG. 6 is an enlarged section along line 6-6 of FIG. 3 with the object "exploded".

DESCRIPTION OF A SPECIFIC EMBODIMENT

Figure 1:
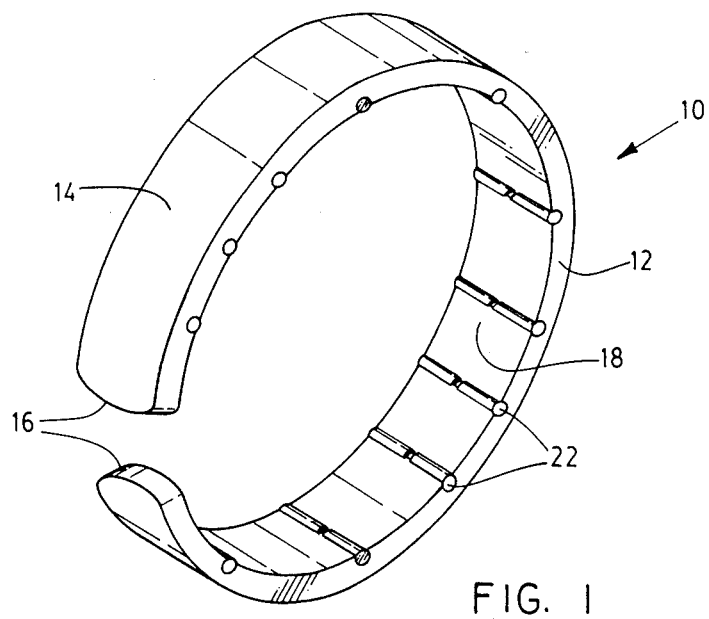
FIG. 1 is a perspective illustration of one embodiment of a mineral applicator according to the invention, showing a plurality of mineral objects in place.
Figure 2:
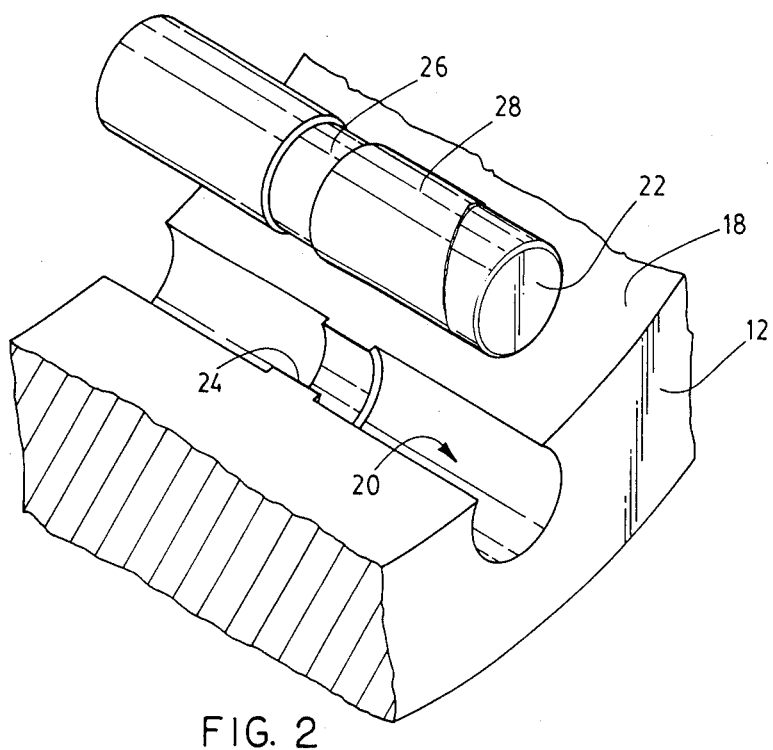
FIG. 2 is a greatly enlarged partial perspective of a portion of the applicator shown in FIG. 1, with a mineral object shown "exploded"

Referring now to FIGS. 1 and 2, it will be apparent that this particular embodiment of the invention is a mineral applicator in the form of a wrist band, indicated generally as 10.

It will however be appreciated that while this is a particularly attractive form of the invention for many purposes, the invention is not restricted solely to the use of a band fitting around the wrist of a user.

Clearly, such a band, given suitable dimensions, could also be fitted around the ankle. It will, of course, be apparent that the invention is not specifically restricted solely to use of a bandlike structure fitting around any part of the body. The invention could equally well comprise a pad (not shown) which could be placed against any part of the body, for example, against the back or stomach, and held in position by tapes, or a belt, or suspended from the neck.

Referring once again to FIG. 1, the holder 10, of this embodiment, will be seen to comprise a elongated holder body 12, typically formed of a resilient thermoplastic material, and contoured to any desired shape on its outer side 14. The holder body 12 is formed in a generally hooplike or semi-circular shape, and defines two free ends 16. The outer surface 14 may be generally smooth and flat as in FIG. 1, or may be contoured to provide any other cross-sectional shape such as semi-cylindrical or the like (not shown) to give the body 12 a more attractive appearance.

An inner or contact surface 18 is provided which is generally smooth and flat, in cross-section, so that it may lie against the portion of the body to which the applicator is applied. Around the inner surface 18 there are a plurality of spaced-apart engagement means which, in this case, comprises generally semi-cylindrical recesses 20. Within the recesses 20, there are provided a plurality of mineral objects 22.

Referring now to FIG. 2, the recesses 20 will be seen to be of regular semi-cylindrical shape along most of their length, and extend transversely of the body 12. Approximately midway, in this embodiment, along the length of each of the recesses 20, there is a locking device in the form of a ridge 24.

Each of the mineral objects 22 is of generally cylindrical shape, and is formed with an annular groove 26, located and dimensioned to receive the ridge 24.

Each of the recesses 20 is dimensioned relative to the dimensions of the mineral objects 22, so that the mineral objects 22 may make a friction fit.

When fitted in place, the objects 22 are thus secured from falling out of the recesses, and cannot slide lengthwise, due to the interengagement of the groove and the ridge.

When positioned in their respective recesses, a portion of each of the objects 22 will extend clear of the inside surface 18 of the holder body 12, and will thus contact and rub against the skin of the user. The bracelet is sufficiently resilient that it can be snapped around the wrist.

The mineral objects 22 may be machined out of rods of different metals, such as steel, copper, zinc and the like. However, more economically, all of the mineral objects may be machined from steel rod, and some of them may then be plated or coated with zinc and some with copper and so on. As shown in FIG. 2, such a coating or plating layer is shown as 28.

A supply of various different mineral objects with different coatings or platings, or possibly with entirely different compositions may be supplied, so as to enable a purchaser to make a selection for himself. Alternatively, the holder 10 may be supplied, together with a predetermined kit of mineral objects, of a variety of different constituents, so that all purchasers may make their own selections.

It will, of course, be appreciated that the mineral objects 22 are not necessarily made of metal. They could be formed of a variety of other minerals. In this sense it will be understood that the term "mineral" will include any substance which may be rubbed against the skin and may be a single mineral or may be a composition of different minerals or elements.

The embodiment of the invention shown in FIGS. 1 and 2 is in the form of a simple bracelet, which will typically have a certain degree of resilience so that it may be snapped around the wrist or ankle, and then will grip more or less firmly and securely in position.

It will, of course, be appreciated however that other embodiments of the invention may achieve a satisfactory result. Thus, as shown in FIGS. 3, 4, 5 and 6, a mineral applicator 30 is shown, which may be in the form of a strap 32, having two free ends, provided with a buckle and tongue fastening indicated generally as 34 and 36, which function in a manner similar, for example, to a watch strap or belt.

The strap 30 may again be formed of thermoplastic material, of a somewhat flexible characteristic.

On the inside surface of the strap 32, a plurality of engagement means may be provided which, in this case, are shown as generally circular recesses 38.

A plurality of mineral objects 40 may be provided fitting within the recesses 38. In this case the objects 40 are of generally flat disc-like shape, similar to coins. In this embodiment, the recesses 38 may be provided with undercut grooves 42, and the objects may be provided with retaining ribs 44. In this way, the objects 40 may be snapped into their respective recesses and retained therein, until removed.

Other means for receiving the numberal objects may be provided however, such as adhesives, pockets, or the like.

It will be appreciated that such a strap-like device 30 may be fastened around the arm or the wrist or the ankle. This may be desirable in some cases, particularly to persons who may prefer to wear a strap-like device, possibly concealed under their clothing, rather than wear a bracelet.

Other materials may be used, and the strap could be of one material, and the free ends of another material, and various fastening systems, such as Velcro (trade mark) could be used.

The person wearing the applicator may select any combination of minerals to be used from time to time according to his or her preference.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A mineral applicator adapted to be worn on the person comprising:
    a holder body with a contact surface adapted to be placed against the skin;
    engagement means on said holder body adjacent said contact surface;
    retaining means for retaining said holder body on the skin; and,
    a plurality of mineral objects engageable with said engagement means, said mineral objects being supported adjacent said contact surface of said holder body, for contacting the skin.

2. A mineral applicator as claimed in claim 1 wherein said holder body is formed around an arc to fit around a portion of the body and wherein said contact surface is on the inside of said arc.

3. A mineral applicator as claimed in claim 1, wherein said engagement means comprise a plurality of recesses formed in said contact surface at spaced intervals.

4. A mineral applicator as claimed in claim 1, wherein said mineral objects comprise a plurality of metal members of identical shape and size, at least some of said members being coated with a coating of copper, and some of said members being coated with a coating of zinc.

5. A mineral applicator as claimed in claim 2 wherein said holder body is flexible, and wherein said retaining means comprise interengagable fastening devices, whereby said applicator can be secured around a portion of the person

* * * * *